(12) United States Patent
Gourdeau et al.

(10) Patent No.: US 6,630,480 B1
(45) Date of Patent: Oct. 7, 2003

(54) METHODS OF TREATING LEUKEMIA

(75) Inventors: Henriette Gourdeau, Montreal (CA); Francis J. Giles, Houston, TX (US)

(73) Assignee: Biochem Pharma Inc., Laval (CA)

( * ) Notice: Subject to any disclaimer, the term of this patent is extended or adjusted under 35 U.S.C. 154(b) by 0 days.

(21) Appl. No.: 09/536,459

(22) Filed: Mar. 28, 2000

Related U.S. Application Data

(60) Provisional application No. 60/126,734, filed on Mar. 29, 2000, and provisional application No. 60/126,813, filed on Mar. 30, 2000.

(51) Int. Cl.[7] .................... A61K 31/505; A61K 31/675

(52) U.S. Cl. .......................................... 514/274; 514/86

(58) Field of Search ................................... 514/274, 86

(56) References Cited

U.S. PATENT DOCUMENTS

| | | |
|---|---|---|
| 5,041,449 A | 8/1991 | Belleau et al. |
| 5,270,315 A | 12/1993 | Belleau et al. |
| 5,817,667 A | 10/1998 | Chu et al. |

*Primary Examiner*—Jerome D. Goldberg

(57) ABSTRACT

The present invention provides a novel method for treating leukemia and more particularly acute myelogenous leukemia (AML) in a host comprising administering to the host a therapeutically effective amount of a compound having the formula I:

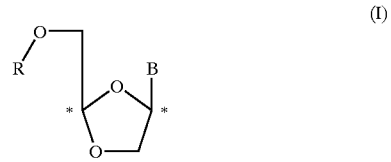

(I)

wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

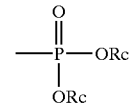

wherein each Rc is independently selected from the group comprising H, $C_{1-6}$ alkyl, $C_{2-6}$ alkenyl, $C_{2-6}$ alkynyl and an hydroxy protecting group; and wherein said compound is substantially in the form of the (−) enantiomer.

36 Claims, No Drawings

METHODS OF TREATING LEUKEMIA

This application claims the benefit of U.S. Provisional Application No. 60/126,734, filed Mar. 29, 2000, and U.S. Provisional Application No. 60/126,813, filed Mar. 30, 2000, both of which are hereby incorporated by reference in their entirety.

FIELD OF THE INVENTION

The present invention relates to methods for treating leukemia, and more particularly, to the use of nucleoside analogues as an effective treatment for acute or chronic myelogenous leukemia.

BACKGROUND OF THE INVENTION

Leukemia is a malignant cancer of the bone marrow and blood. It is characterized by the uncontrolled growth of blood cells. The common types of leukemia are divided into four categories: acute or chronic myelogenous, involving the myeloid elements of the bone marrow (white cells, red cells, megakaryocytes) and acute or chronic lymphocytic, involving the cells of the lymphoid lineage.

Acute leukemia is a rapidly progressing disease that results in the massive accumulation of immature, functionless cells (blasts) in the marrow and blood. The marrow often can no longer produce enough normal red and white blood cells and platelets. Anemia, a deficiency of red cells, develops in virtually all leukemia patients. The lack of normal white cells impairs the body's ability to fight infections. A shortage of platelets results in bruising and easy bleeding. In contrast, chronic leukemia progresses more slowly and leads to unregulated proliferation and hence marked overexpansion of a spectrum of mature (differentiated) cells. In general, acute leukemia, unlike the chronic form, is potentially curable by elimination of the neoplastic clone.

It is estimated that there will be 28,700 new cases of leukemia in the United States this year; about equal proportions are acute leukemia and chronic types. Most cases occur in older adults. Leukemia is expected to strike ten times as many adults as children in 1998. (About 26,500 cases compared to 2,200 in children) More than half of all cases of leukemia occur in persons over 60. The most common types of leukemia in adults are acute myelogenous leukemia (AML) with an estimated 9,400 new cases annually, chronic lymphocytic leukemia (CLL), with some 7,300 new cases this year and chronic myeloid leukemia (CML). The most common type of leukemia in children is acute lymphocytic leukemia (ALL).

Standard treatment for leukemia usually involves chemotherapy and/or bone marrow transplantation and/or radiation therapy.

The two major types of bone marrow transplants are autologus (uses the patient's own marrow) and allogeneic (uses marrow from a compatible donor). Radiation therapy, which involves the use of high-energy rays, is usually given before bone marrow transplantation to kill all leukemic cells.

Chemotherapy in leukemia usually involves a combination of two or more anti-cancer drugs. Approximately 40 different drugs are now being used in the treatment of leukemia. Some common combinations include cytarabine with either doxorubicin or daunorubicin or mitoxantrone or thioguanine, mercaptopurine with methotrexate, mitroxantrone with etoposide, asparaginase with vincristine, daunorubicin and prednisone, cyclophosphamide with vincristine, cytarabine and prednisone, cyclophosphamide with vincristine and prednisone, daunorubicin with cytarabine and thioguanine and daunorubicin with vincristine and prednisone.

New treatments for leukemia also include the reversal of multidrug resistance, involving the use of agents which decrease the mechanisms allowing the malignant cells to escape the damaging effects of the chemotherapeutic agent (and leads to refractoriness or relapses); and biological therapy, involving the use of substances known as biological response modifiers (BRMs). These substances are normally produced in small amounts as part of the body's natural response to cancer or other diseases. Types of BRMs include monoclonal antibodies, in which toxins are attached to antibodies that react with the complementary antigen carried by the malignant cells; and cytokines (e.g. interferons, interleukins, colony-stimulating factors CSFs) which are naturally occuring chemicals that stimulate blood cell production and help restore blood cell counts more rapidly after treatment. Examples of these drugs include multidrug resistance reversing agent PSC 833, the monoclonal antibody Rituxan and the following cytokines: Erythropoetin and Epoetin, which stimulate the production of red cells; G-CSF, GM-CSF, filgrastim, and Sargramostim which stimulate the production of white cells; and thrombopoietin, which stimulate the production of platelets.

Many nucleoside analogues have been found to possess anticancer cancer activity. Cytarabine, Fludarabine, Gemcitabine and Cladribine are some examples of nucleoside analogues which are currently important drugs in the treatment of leukemia.

(−)-β-L-Dioxolane-Cytidine(β-L-OddC) is also a nucleoside analogue that was first described as an antiviral agent by Belleau et al. (EP 337713) and has been shown to have potent antitumor activity (K. L. Grove et al., Cancer Res., 55(14), 3008–11, 1995; K. L. Grove et al., Cancer Res., 56(18), 4187–4191, 1996, K. L. Grove et al., Nucleosides Nucleotides, 16:1229–33, 1997; S. A Kadhim et al., Can. Cancer Res., 57(21), 4803–10, 1997).

Treatment of leukemia is very complex and depends upon the type of leukemia. Tremendous clinical variability among remissions is also observed in leukemic patients, even those that occur after one course of therapy. Patients who are resistant to therapy have very short survival times, regardless of when the resistance occurs. Despite improvements in outcome with current treatment programs, the need to discover novel agents for the treatment of all types of leukemia continues.

SUMMARY OD THE INVENTION

The present invention provides a novel method for treating leukemia in a host comprising administering a therapeutically effective amount of a compound having the formula I:

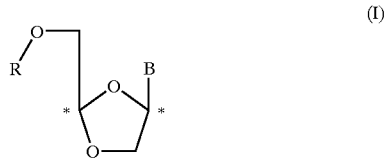

wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

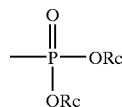

wherein each Rc is independently selected from the group comprising H, $C_{1-6}$ alkyl, $C_{2-6}$ alkenyl, $C_{2-6}$ alkynyl and an hydroxy protecting group; and wherein said compound is substantially in the form of the (−) enantiomer.

In another embodiment, there is provided a method for treating leukemia in a host comprising administering to the host a therapeutically effective amount of at least one compound according to formula I and at least one further therapeutic agent selected from the group comprising chemotherapeutic agents; multidrug resistance reversing agents; and biological response modifiers.

Still another embodiment, there is provided a pharmaceutical composition for treating leukemia comprising at least one compound according to formula I together with at least one pharmaceutically acceptable carrier or excipient.

In another embodiment, there is provided a pharmaceutical composition for treating leukemia comprising at least one compound according to formula I and at least one further therapeutic agent selected from the group comprising chemotherapeutic agents; multidrug resistance reversing agents; and biological response modifiers.

In another embodiment of the invention is the use of a compound according to formula I for the manufacture of a medicament for treating leukemia.

DETAILED DESCRIPTION OF THE INVENTION

The present invention provides a novel method for treating leukemia in a host comprising administering a therapeutically effective amount of a compound having the formula I:

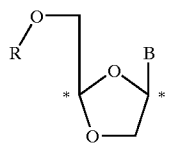

(I)

wherein B is cytosine or 5-fluorocytosine and R is selected from the group comprising H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

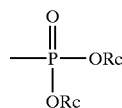

wherein each Rc is independently selected from the group comprising H, $C_{1-6}$ alkyl, $C_{2-6}$ alkenyl, $C_{2-6}$ alkynyl and an hydroxy protecting group; and wherein said compound is substantially in the form of the (−) enantiomer.

In another embodiment of the invention, R is H.
In another embodiment, B is cytosine.

Alternatively, in another embodiment, B is 5-fluorocytosine.

In one embodiment, a compound of formula I is (−)-β-L-Dioxolane-Cytidine (β-L-oddC).

In another embodiment, a compound of formula I is (−)-β-Dioxolane-5-fluoro-Cytidine (5-L-FddC).

It will be appreciated by those skilled in the art that the compounds of formula (I) contain at least two chiral centres which are marked by an asterisk (*) on formula (I). The compounds of formula (I) thus exist in the form of two different optical isomers (i.e. (+) or (−) enantiomers or β-L and β-D). All such enantiomers and mixtures thereof including racemic mixtures are included within the scope of the invention. The single optical isomer or enantiomer can be obtained by method well known in the art, such as chiral HPLC, enzymatic resolution and the use of chiral auxiliary.

According to one embodiment, compounds of formula I of the present invention are provided substantially in the form of the (−) enantiomer.

By "substantially" is meant that there is more of the (−) enantiomer then the (+) enantiomer.

In another embodiment, the compounds of formula I of the present invention are at least 95% free of the corresponding (+) enantiomer.

In another embodiment, the compounds of formula I of the present invention are at least 97% free of the corresponding (+) enantiomer.

Still in another embodiment, the compounds of formula I of the present invention are at least 99% free of the corresponding (+) enantiomer.

There is also provided pharmaceutically acceptable salts of the compounds of formula I of the present invention. By the term pharmaceutically acceptable salts of the compounds of formula (I) are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, citric, methanesulphonic, formic, benzoic, malonic, naphthalene-2-sulphonic and benzenesulphonic acids.

Salts derived from appropriate bases include alkali metal (e.g. sodium), alkaline earth metal (e.g. magnesium), ammonium and $NR_4^+$ (where R is $C_{1-4}$ alkyl) salts.

As used in this application, the term "alkyl" represents an unsubstituted or substituted (by a halogen, nitro, $CONH_2$, COOH, O—$C_{1-6}$ alkyl, O—$C_{2-6}$ alkenyl, O—$C_{2-6}$ alkynyl, hydroxyl, amino, or COOQ, wherein Q is $C_{1-6}$ alkyl; $C_{2-6}$ alkenyl; $C_{2-6}$ alkynyl) straight chain, branched chain or cyclic hydrocarbon moiety (e.g. isopropyl, ethyl, fluorohexyl or cyclopropyl). The term alkyl is also meant to include alkyls in which one or more hydrogen atoms is replaced by an halogen, more preferably, the halogen is fluoro (e.g. $CF_3$— or $CF_3CH_2$—).

The terms "alkenyl" and "alkynyl" represent an alkyl containing at least one unsaturated group (e.g. allyl).

The term "hydroxy protecting group" is well known in the field of organic chemistry. Such protecting groups may be found in T. Greene, *Protective Groups In Organic Synthesis*, (John Wiley & Sons, 1981). Example of hydroxy protecting groups include but are not limited to acetyl-2-thioethyl ester, pivaloyloxymethyl ester and isopropyloxycarbonyloxymethyl ester.

The term "aryl" represent an unsaturated carbocyclic moiety, optionally mono- or di-substituted with OH, SH, amino, halogen or $C_{1-6}$ alkyl, and optionally substituted by at least one heteroatom (e.g. N, O, or S).

In one embodiment, the present invention provides a method for treating myelogenous leukemia.

In another embodiment, the present invention provides a novel method for treating acute myelogenous leukemia.

In another embodiment, the present invention provides a novel method for treating chronic myelogenous leukemia.

Still in another embodiment, the present invention provides a novel method for treating multidrug resistant leukemia.

The term "leukemia" represent acute myelogenous leukemia (AML), chronic myelogenous leukemia (CML), acute lymphocytic leukemia (ALL), chronic lymphocytic leukemia (CLL), hairy cell leukemia (HCL) and all subtypes of these leukemias which are defined by morphological, histochemical and immunological techniques that are well known by those skilled in the art.

The term "myelogenous leukemia" represent both acute and chronic myelogenous leukemias (AML, CML) which involve the myeloid elements of the bone marrow (e.g. white cells, red cells and megakaryocytes) and includes all subtypes which are defined by morphological, histochemical and immunological techniques that are well known by those skilled in the art.

The term "multidrug resistant leukemia" represent a leukemia which is non responsive to treatment with chemotherapeutic agents.

The term "host" represent any mammals including humans.

In one embodiment, the host is human.

According to one embodiment, the patient treated has been previously treated with cytarabine (Ara-C). The patient is treated according to any one of the method set forth herein.

According to one embodiment, the patient that has been previously treated is resistant to cytarabine (Ara-C). The patient is treated according to any one of the methods set forth herein.

According to another embodiment, the patient is refractory to Ara-C.

According to one embodiment, it will be appreciated that the amount of a compound of formula I of the present invention required for use in treatment will vary not only with the particular compound selected but also with the route of administration, the nature of the condition for which treatment is required and the age and condition of the patient and will be ultimately at the discretion of the attendant physician or veterinarian. In general however a suitable dose will be in the range of from about 0.01 to about 750 mg/kg of body weight per day, preferably in the range of 0.5 to 60 mg/kg/day, most preferably in the range of 1 to 20 mg/kg/day.

The desired dose according to one embodiment is conveniently presented in a single dose or as divided dose administered at appropriate intervals, for example as two, three, four or more doses per day.

In another embodiment, the compound is conveniently administered in unit dosage form; for example containing 10 to 1500 mg, conveniently 20 to 1000 mg, most conveniently 50 to 700 mg of active ingredient per unit dosage form.

According to another embodiment of the present invention, the active ingredient is administered to achieve peak plasma concentrations of the active compound of from about 1 to about 75 $\mu$M, preferably about 2 to 50 $\mu$M, most preferably about 3 to about 30 $\mu$M. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

While it is possible that, for use in therapy, a compound of formula I of the present invention may be administered as the raw chemical, it is preferable according to one embodiment of the invention, to present the active ingredient as a pharmaceutical formulation. The embodiment of the invention thus further provides a pharmaceutical formulation comprising a compound of formula (I) or a pharmaceutically acceptable salt thereof together with one or more pharmaceutically acceptable carriers therefor and, optionally, other therapeutic and/or prophylactic ingredients. The carrier(s) must be "acceptable" in the sense of being compatible with the other ingredients of the formulation and not deleterious to the recipient thereof.

According to one embodiment of the present invention, pharmaceutical formulations include but are not limited to those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods according to this embodiment include the step of bringing into association the active compound with liquid carriers or finely divided solid carriers or both and then, if necessary, shaping the product into the desired formulation.

According to another embodiment, pharmaceutical formulation suitable for oral administration are conveniently presented as discrete units such as capsules, cachets or tablets each containing a predetermined amount of the active ingredient; as a powder or granules. In another embodiment, the formulation is presented as a solution, a suspension or as an emulsion. Still in another embodiment, the active ingredient is presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds of formula I according to an embodiment of the present invention are formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing an/or dispersing agents. Alternatively, the active ingredient may be in powder form, obtained by aseptic isolation of sterile solid or by lyophilisation from solution, for constitution with a suitable vehicle, e.g. sterile, pyrogen-free water, before use.

For topical administration to the epidermis, the compounds of formula I, according to one embodiment of the present invention, are formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or colouring agents.

Formulations suitable for topical administration in the mouth include lozenges comprising active ingredient in a flavoured base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical formulations suitable for rectal administration wherein the carrier is a solid. In another embodiment, they are presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

According to one embodiment, the formulations suitable for vaginal administration are presented as pessaries, tampons, creams, gels, pastes, foams or sprays containing in addition to the active ingredient such carriers as are known in the art to be appropriate.

For intra-nasal administration the compounds, in one embodiment of the invention, are used as a liquid spray or dispersible powder or in the form of drops. Drops may be formulated with an aqueous or non-aqueous base also comprising one more dispersing agents, solubilising agents or suspending agents. Liquid sprays are conveniently delivered from pressurized packs.

For administration by inhalation the compounds, according to one embodiment of the invention are conveniently delivered from an insufflator, nebulizer or a pressurized pack or other convenient means of delivering an aerosol spray. In another embodiment, pressurized packs comprise a suitable propellant such as dichlorodifluoromethane, trichlorofluoromethane, dichlorotetrafluoroethane, carbon dioxide or other suitable gas. In another embodiment, the dosage unit in the pressurized aerosol is determined by providing a valve to deliver a metered amount.

Alternatively, in another embodiment, for administration by inhalation or insufflation, the compounds of formula I according to the present invention are in the form of a dry powder composition, for example a powder mix of the compound and a suitable powder base such as lactose or starch. In another embodiment, the powder composition is presented in unit dosage form in, for example, capsules or cartridges or e.g. gelatin or blister packs from which the powder may be administered with the aid of an inhalator or insufflator.

In one embodiment, the above described formulations are adapted to give sustained release of the active ingredient.

In another embodiment, there is provided a method for treating leukemia in a host comprising administering to the host a therapeutically effective amount of at least one compound according to formula I and at least one further therapeutic agent selected from the group comprising chemotherapeutic agents; multidrug resistance reversing agents; and biological response modifiers.

In another embodiment, the chemotherapeutic agents are selected from the group consisting of Asparaginase, Bleomycin, Busulfan, Carmustine, Chlorambucil, Cladribine, Cyclophosphamide, Cytarabine, Dacarbazine, Daunorubicin, Doxorubicin, Etoposide, Fludarabine, Gemcitabine, Hydroxyurea, Idarubicin, Ifosfamide, Lomustine, Mechlorethamine, Melphalan, Mercaptopurine, Methotrexate, Mitomycin, Mitoxantrone, Pentostatin, Procarbazine, 6-Thioguanine, Topotecan, Vinblastine, Vincristine, Dexamethasone, Retinoic acid and Prednisone.

In another embodiment, the chemotherapeutic agents are selected from the group consisting of Cytarabine, Etoposide, Mitoxantron, Cyclophosphamide, Retinoic acid, Daunorubicin, Doxorubicin and Idarubicin.

Still in another embodiment, the chemotherapeutic agent is Doxorubicin.

In one embodiment, the multidrug resistance reversing agent is PSC 833.

In another embodiment, the biological response modifiers are selected from the group consisting of monoclonal antibodies and cytokines.

In another embodiment, the cytokines are selected from the group consisting of interferons, interleukins and colony-stimulating factors.

In another embodiment, the biological response modifiers are selected from the group consisting of Rituxan, CMA-676, Interferon-alpha recombinant, Interleukin-2, Interleukin-3, Erythropoetin, Epoetin, G-CSF, GM-CSF, Filgrastim, Sargramostim and Thrombopoietin.

In one embodiment of the present invention, the combinations referred to above are conveniently presented for use in the form of a pharmaceutical composition comprising a combination as defined above together with a pharmaceutically acceptable carrier.

In another embodiment, the individual components of such combinations are administered either sequentially or simultaneously in separate or combined pharmaceutical formulations.

In one embodiment of the present invention, when the compound of formula I or a pharmaceutically acceptable salt thereof is used in combination with a second therapeutic agent, the dose of each compound is either the same as or differ from that when the compound is used alone. Appropriate doses will be readily appreciated by those skilled in the art.

The compounds of formula I of the present invention can be prepared as follows.

The following examples are provided to illustrate various embodiments of the present invention and shall not be considered as limiting in scope. Example 1

Preparation of β-L-oddC.

Scheme 1

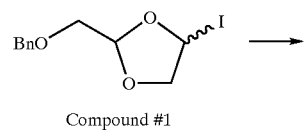

Compound #1

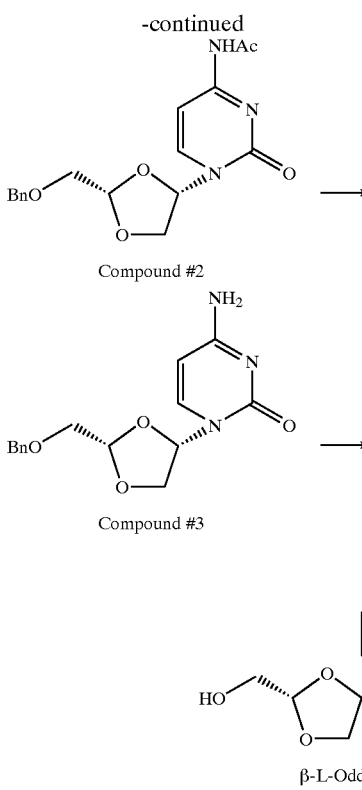

Compound #2 (NHAc, BnO)

Compound #3 (NH₂, BnO)

β-L-OddC (NH₂, HO)

Compound #1: 2S-Benzyloxymethyl-4R-iodo-1,3 Dioxolane and 2SBenzyloxymethyl-4S-iodo-1,3 Dioxolane A mixture consisting of 2S-benzyloxymethyl-4S acetoxy-1,3 dioxolane and 2S-benzyloxymethyl-4R-acetoxy-1,3 dioxolane in 1:2 ratio (6 g; 23.8 mmol) was dried by azeotropic distillation with toluene in vacuo. After removal of toluene, the residual oil was dissolved in dry dichloromethane (60 ml) and iodotrimethylsilane (3.55 ml; 1.05 eq) was added at −78° C., under vigorous stirring. The dry-ice/acetone bath was removed after addition and the mixture was allowed to warm up to room temperature (15 min.). The $^1$H NMR indicated the formation of 2S-benzyloxymethyl-4R-iodo-1,3-dioxolane and 2S-benzyloxymethyl-4S-iodo-1,3 dioxolane.

$^1$H NMR (300 MHz, CDCl$_3$) δ3.65–4.25 (2H,m); 4.50–4.75 (4H, m) 5.40–5.55 (1H, overlapping triplets); 6.60–6.85 (1H, d of d); 7.20–7.32 (5H,m)

Compound #2: β-L-5'-Benzyl-2'-deoxy-3'-oxa-N-4-acetyl-cytidine

The previously prepared iodo intermediate (Compound #1) in dichloromethane, was cooled down to −78° C. Persylilated N-acetyl cytosine (1.1 eq) formed by reflux in 1,1,1,3,3,3-hexamethyl disilazane (HMDS) and ammonium sulphate followed by evaporation of HMDS was dissolved in 30 ml of dichloromethane and was added to the iodo intermediate. The reaction mixture was maintained at −78° C. for 1.5 hours then poured onto aqueous sodium bicarbonate and extracted with dichloromethane (2×25 ml).

The organic phase was dried over sodium sulphate, the solid was removed by filtration and the solvent was evaporated in vacuo to produce 8.1 g of a crude mixture. Based on $^1$H NMR analysis, the β-L-5'-benzyl-2'-deoxy-3'-oxacytidine and its α-L isomer were formed in a ratio of 5:1 respectively. This crude mixture was separated by chromatography on silica-gel (5% MeOH in EtOAc) to generate the pure β-L (cis) isomer (4.48 g). Alternatively, recrystallization of the mixture from ethanol produces 4.92 g of pure β isomer and 3.18 g of a mixture of β and a-isomers in a ratio of 1:1. $^1$H NMR (300 MHz, CDCl$_3$) δ2.20 (3H,S,Ac); 3.87 (2H, m, H-5'), 4.25 (2H,m,H-2'); 4.65 (2H,dd,OCH$_2$Ph); 5.18 (1H,t,H-4'); 6.23 (1H,m,H-1'); 7.12 (1H,d,H-5); 7.30–7.50 (5H,m,Ph); 8.45 (2H,m,NH+H-6)

Compound #3: β-L-5'-Benzyloxy-2'-deoxy-3'-oxacytidine

The protected β-L isomer (4.4 g) (Compound #2) was suspended in saturated methanolic ammonia (250 ml) and stirred at room temperature for 18 hours in a closed vessel. The solvents were then removed in vacuo to afford the deacetylated nucleoside in pure form.

$^1$H NMR (300 MHz, CDCl$_3$) δ3.85 (2H,m,H-5'); 4.20 (2H,m,H-2'); 4.65 (2H,dd,OCH$_2$Ph); 5.18 (1H,t,H-4'); 5.43 (1H,d,H-5); 5.50–5.90 (2H,br.S,NH$_2$); 6.28 (1H,m,H-1'); 7.35–7.45 (5H,m,Ph); 7.95 (1H,d,H-6).

Compound #4: β-L-OddC

β-L-5'-Benzyl-2'-deoxy-3'-oxacytidine (Compound #3) was dissolved in EtOH (200 ml) followed by addition of cyclohexene (6 ml) and palladium oxide (0.8 g). The reaction mixture was refluxed for 7 hours then it was cooled and filtered to remove solids. The solvents were removed from the filtrate by vacuum distillation. The crude product was purified by flash chromatography on silica-gel (5% MeOH in EtOAc) to yield a white solid (b-L-OddC)(2.33 g; 86% overall yield, $\alpha_D^{22}$=−46.70° (c=0.285; MeOH) m.p.= 192–194° C.). $^1$H NMR (300 MHz, DMSO-d$_6$) δ3.63 (2H, dd,H-5'); 4.06 (2H,m,H-2'); 4.92 (1H,t,H-4'); 5.14 (1H,t, OH); 5.70 (1H,d,H-5); 6.16 (2H,dd,H-1'); 7.11–7.20 (2H, brS,NH$_2$); 7.80 (1H,d,H-6) $^{13}$C NMR (75 MHz, DMSO-d$_6$) δ59.5 (C-2'); 70.72 (C-5'); 81.34 (C-4'); 93.49 (C-1'); 104.49 (C-5); 140.35 (C-4); 156.12 (C-6); 165.43 (C-2).

EXAMPLE 2

Evaluation of β-L-oddC in Patients With Advanced Leukemia

The study involved treatment of patients with advanced leukemia that had been previously treated with Citarabine (Ara-C). The previous treatment with Ara-C had failed to stop progression of the disease. Twelve patients were treated with an initial course at daily doses of 0.72 mg/m2 (4 patients), 1.08 mg/m² (5 patients), 1.62 mg/m² (3 patients) given as a daily infusion over 30 minutes for 5 consecutive days. Five patients were treated with second courses at daily doses of 1.08 mg/m² (3 patients), 1.62 mg/m² (2 patients) given over 5 consecutive days as above. 1 patient was treated with a 3$^{rd}$ 5 day course at the 2.43 mg/m² daily dose level. 4 patients (2 each at the 1.08 mg/m² and 1,62 mg/m² levels) have shown a transient decrease in peripheral blood and bone marrow blasts. Of these four patients, three had acute mylogenous leukemia and one had chronic mylogenous leukemia.

EXAMPLE 3

β-L-OddC/doxorubicine Combination Study in a Human Leukemia (HL60) Xenograft Model A study was conducted to evaluate the synergistic or additive therapeutic effect of β-L-OddC in combination with the currently known anticancer agent Doxorubicin. The model that was utilized is a survival model consisting of female SCID mice which are inoculated in the abdomen region (i.p.) with $15 \times 10^6$ HL60 cells in log phase growth. This corresponds to day 0 of the experiment. Administration of anti-cancer drug is started 10 days after tumor cell inoculation.

10 animals were used per group for β-L-oddC alone, Doxorubicin alone and the combination of β-L-oddC with Doxorubicin. Each groups received the drugs alone or in combination intravenously once daily for 5 consecutive days.

Augmentation of survival time was calculated by substracting from the median survival time of group two to six, which corresponds to the day when the fifth mouse dies, the median survival time of control group 1 and multiplying by 100.

In Table 1 below, we observe that the best treatment corresponds to the combination of β-L-oddC with Doxorubicin at a dose of 2 mg/Kg. This combination extends the survival time of the mice substantially compared to either single agents β-L-oddC and Doxorubicin.

TABLE 1

COMBINATION STUDY β-L-OddC/DOXORUBICIN IN HUMAN LEUKEMIA (HL60)

| Group of | Combination | Augmentation Survival Time |
|---|---|---|
| 1 | Saline i.p. | |
| 2 | β-L-OddC 1 mg/kg | 55% |
| 3 | Doxorubicin 0.2 mg/kg | 25% |
| 4 | β-L-OddC 1 mg/kg + Doxorubicin 0.2 mg/kg | 55% |
| 5 | Doxorubicin 2 mg/kg | 50% |
| 6 | β-L-OddC 1 mg/kg. + Doxorubicin 2 mg/kg | 100% |

We claim:

1. A method for treating a patient with leukemia comprising;
   administering to said patient having chronic myelogenous leukemia or acute myelogenous leukemia, a therapeutically effective amount of a compound having the formula I:

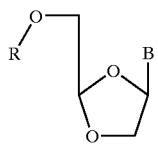

(I)

wherein B is cytosine or 5-fluorocytosine and R is selected from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

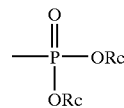

wherein each Rc is independently selected from H, $C_{1-6}$ alkyl, $C_{2-6}$ alkenyl, $C_{2-6}$ alkynyl and hydroxy protecting groups;
   wherein said compound is substantially in the form of the (−) enantiomer;
   wherein the step of administering comprises administering to a patient that has been previously treated with Ara-C; and
   wherein said compound of formula I is at least 95% free of the (+) form.

2. The method according to claim 1, wherein R is H.
3. The method according to claim 1, wherein B is cytosine.
4. The method according to claim 3, wherein said compound of formula I is at least 97% free of the (+) form.
5. The method according to claim 3, wherein said compound of formula I is at least 99% free of the (+) form.
6. The method according to claim 1, wherein R is H and B is cytosine.
7. The method according to claim 6, wherein said compound of formula I is at least 97% free of the (+) form.
8. The method according to claim 6, wherein said compound of formula I is at least 99% free of the (+) form.
9. The method of claim 1, wherein the leukemia is a chronic myelogenous leukemia.
10. The method of claim 1, wherein the leukemia is an acute myelogenous leukemia.
11. The method according to claim 1, wherein said compound of formula I is at least 97% free of the (+) form.
12. The method according to claim 1, wherein said compound of formula I is at least 99% free of the (+) form.
13. A method according to claim 1, wherein said hydroxy protecting groups are acetyl-2-thioethyl ester, pivaloyloxymethyl ester, and isopropyloxycarbonyloxymethyl ester.
14. A method according to claim 1, wherein said compound is administered in an amount of 0.1–750 mg/kg of bodyweight per day.
15. A method according to claim 1, wherein said compound is administered in an amount of 0.5–60 mg/kg of bodyweight per day.
16. A method according to claim 1, wherein said compound is administered in an amount of 1–20 mg/kg of bodyweight per day.
17. A method according to claim 1, wherein said compound is administered in a daily amount of 1.08 mg/m$^2$–1.62 mg/m$^2$.
18. A method according to claim 1, wherein said compound is administered in a unit dosage form containing 10–1500 mg of said compound.
19. A method according to claim 1, wherein said compound is administered in a unit dosage form containing 20–1000 mg of said compound.
20. A method according to claim 1, wherein said compound is administered in a unit dosage form containing 50–700 mg of said compound.
21. A method for treating a patient with leukemia comprising:
   administering to said patient having chronic myelogenous leukemia or acute myelogenous leukemia, a therapeutically effective amount of a compound having the formula I:

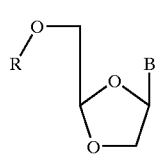

(I)

wherein B is cytosine or 5-fluorocytosine and R is selected from H, monophosphate, diphosphate, triphosphate, carbonyl substituted with a $C_{1-6}$ alkyl, $C_{2-6}$ alkenyl, $C_{2-6}$ alkynyl, $C_{6-10}$ aryl, and

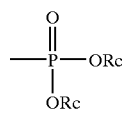

wherein each Rc is independently selected from H, $C_{1-6}$ alkyl, $C_{2-6}$ alkenyl, $C_{2-6}$ alkynyl and hydroxy protecting groups;
wherein said compound is substantially in the form of the (−) enantiomer;
wherein said patient is suffering from a leukemia which is non-responsive to treatment with other chemotherapeutic agents; and
wherein said compound of formula I is at least 95% free of the (+) form.

22. The method according to claim 21, wherein R is H.

23. The method according to claim 21, wherein B is cytosine.

24. The method according to claim 21, wherein R is H and B is cytosine.

25. The method according to claim 24, wherein said compound of formula I is at least 97% free of the (+) form.

26. The method according to claim 24, wherein said compound of formula I is at least 99% free of the (+) form.

27. The method according to claim 21, wherein said compound of formula I is at least 97% free of the (+) form.

28. The method according to claim 21, wherein said compound of formula I is at least 99% free of the (+) form.

29. A method according to claim 21, wherein said hydroxy protecting groups are acetyl-2-thioethyl ester, pivaloyloxymethyl ester, and isopropyloxycarbonyloxymethyl ester.

30. A method according to claim 21, wherein said compound is administered in an amount of 0.1–750 mg/kg of bodyweight per day.

31. A method according to claim 21, wherein said compound is administered in an amount of 0.5–60 mg/kg of bodyweight per day.

32. A method according to claim 21, wherein said compound is administered in an amount of 1–20 mg/kg of bodyweight per day.

33. A method according to claim 21, wherein said compound is administered in a daily amount of 1.08 mg/m$^2$–1.62 mg/m$^2$.

34. A method according to claim 21, wherein said compound is administered in a unit dosage form containing 10–1500 mg of said compound.

35. A method according to claim 21, wherein said compound is administered in a unit dosage form containing 20–1000 mg of said compound.

36. A method according to claim 21, wherein said compound is administered in a unit dosage form containing 50–700 mg of said compound.

* * * * *

UNITED STATES PATENT AND TRADEMARK OFFICE
CERTIFICATE OF CORRECTION

PATENT NO. : 6,630,480 B1
DATED : October 7, 2003
INVENTOR(S) : Gourdeau et al.

It is certified that error appears in the above-identified patent and that said Letters Patent is hereby corrected as shown below:

Title page,
Item [60], delete "2000" and insert -- 1999 -- (both occurrences).

Column 1,
Lines 4 and 6, delete "2000" and insert -- 1999 --.

Signed and Sealed this

Sixth Day of April, 2004

JON W. DUDAS
*Acting Director of the United States Patent and Trademark Office*